United States Patent
Ruhl et al.

(10) Patent No.: US 7,582,258 B2
(45) Date of Patent: Sep. 1, 2009

(54) BODY FLUID TESTING DEVICE

(75) Inventors: Werner Ruhl, Limburgerhof (DE); Hugo Schrem, Weinheim (DE); Volker Zimmer, Morbach (DE); Klaus Zimmer, legal representative, Morbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 512 days.

(21) Appl. No.: 11/165,115

(22) Filed: Jun. 23, 2005

(65) Prior Publication Data
US 2005/0232815 A1  Oct. 20, 2005

Related U.S. Application Data

(63) Continuation of application No. PCT/EP03/14708, filed on Dec. 22, 2003.

(30) Foreign Application Priority Data
Dec. 23, 2002  (EP) .................................. 02028894

(51) Int. Cl.
| | |
|---|---|
| G01N 21/00 | (2006.01) |
| B65D 81/00 | (2006.01) |
| B01J 19/30 | (2006.01) |
| B65D 85/04 | (2006.01) |
| B65H 75/30 | (2006.01) |
| G01B 3/10 | (2006.01) |

(52) U.S. Cl. ........................ 422/66; 422/67; 600/584; 206/53; 242/381.2; 33/760

(58) Field of Classification Search ............... 422/66, 422/310, 67; 600/584; 206/53; 242/381.2; 33/760
See application file for complete search history.

(56) References Cited

U.S. PATENT DOCUMENTS

| 2,714,890 A | 8/1955 | Vang |
| 3,086,288 A | 4/1963 | Balamuth et al. |
| 3,208,452 A | 9/1965 | Stern |
| 3,298,789 A | 1/1967 | Mast |

(Continued)

FOREIGN PATENT DOCUMENTS

DE  28 03 345 B1  6/1979

(Continued)

*Primary Examiner*—Jill Warden
*Assistant Examiner*—Lore Jarrett
(74) *Attorney, Agent, or Firm*—Woodard, Emhardt, Moriarty, McNett & Henry LLP

(57) ABSTRACT

Body fluid testing device for analyzing a body fluid comprises a test media tape adapted to collect the body fluid. The test media tape comprises a tape and test media portions. A free tape portion without test medium is located between successive test media portions. The testing device further comprises a supply portion. The supply portion comprises a housing in which uncontaminated test media tape is contained. The housing further has an opening for withdrawing test media tape from the housing. The testing device further has a sealing means for closing the opening against the surrounding. A free tape portion of the test media tape is located between a wall of the housing and the sealing means when the sealing means closes the opening. Further aspects concern a test media cassette with sealing means and a method for providing test media while holding them sealed against humidity during onboard storage.

11 Claims, 8 Drawing Sheets

U.S. PATENT DOCUMENTS

Figure 1:
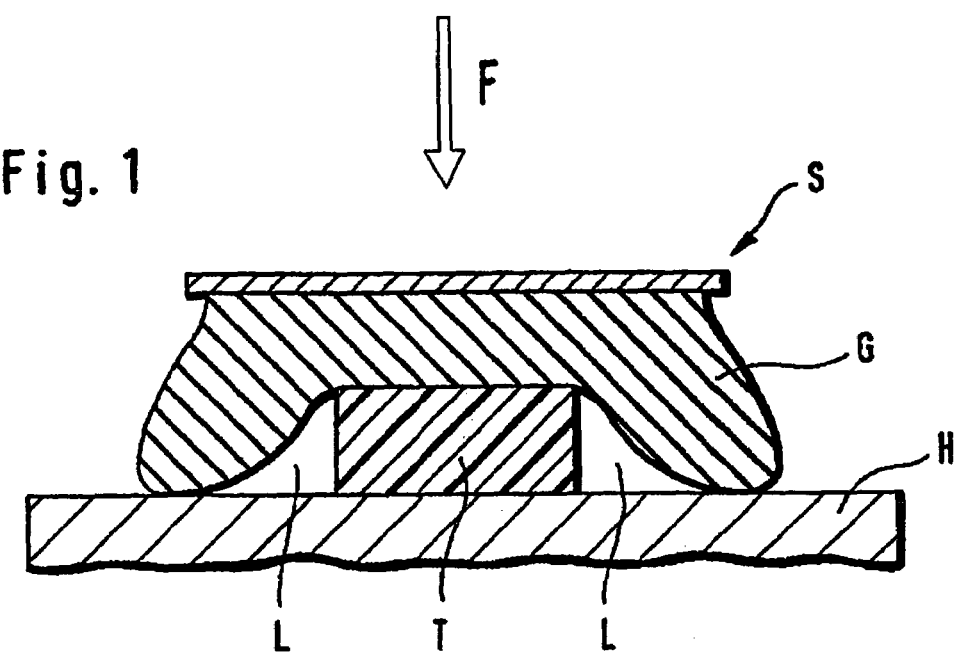

| | | | |
|---|---|---|---|
| 3,673,475 A | 6/1972 | Britton, Jr. | |
| 3,802,842 A | 4/1974 | Lange et al. | |
| 3,832,776 A | 9/1974 | Sawyer | |
| 4,061,468 A | 12/1977 | Lange et al. | |
| 4,065,263 A * | 12/1977 | Woodbridge, III | 422/57 |
| 4,077,406 A | 3/1978 | Sandhage et al. | |
| 4,154,228 A | 5/1979 | Feldstein et al. | |
| 4,203,446 A | 5/1980 | Hofert et al. | |
| 4,218,421 A | 8/1980 | Mack, Jr. et al. | |
| 4,223,674 A | 9/1980 | Fluent et al. | |
| 4,230,118 A | 10/1980 | Holman et al. | |
| 4,356,826 A | 11/1982 | Kubota | |
| 4,449,529 A | 5/1984 | Burns et al. | |
| 4,462,405 A | 7/1984 | Erhlich | |
| 4,490,465 A | 12/1984 | Limbach et al. | |
| 4,518,384 A | 5/1985 | Tarello et al. | |
| 4,535,773 A | 8/1985 | Yoon | |
| 4,553,541 A | 11/1985 | Burns et al. | |
| 4,627,445 A | 12/1986 | Garcia et al. | |
| 4,637,403 A | 1/1987 | Garcia et al. | |
| 4,653,513 A | 3/1987 | Dombrowski | |
| 4,750,489 A | 6/1988 | Berkman et al. | |
| 4,787,398 A | 11/1988 | Garcia et al. | |
| 4,794,926 A | 1/1989 | Munsch et al. | |
| 4,823,806 A | 4/1989 | Bajada | |
| 4,924,879 A | 5/1990 | O'Brien | |
| 4,954,319 A * | 9/1990 | Koizumi et al. | 422/67 |
| 4,971,774 A * | 11/1990 | Schwanke et al. | 422/310 |
| 4,994,068 A | 2/1991 | Hufnagle | |
| 4,995,402 A | 2/1991 | Smith et al. | |
| 5,009,850 A | 4/1991 | Bell | |
| 5,029,583 A | 7/1991 | Meserol et al. | |
| 5,035,704 A | 7/1991 | Lambert et al. | |
| 5,047,044 A | 9/1991 | Smith et al. | |
| 5,053,199 A | 10/1991 | Keiser et al. | |
| 5,077,010 A | 12/1991 | Ishizaka et al. | |
| 5,097,810 A | 3/1992 | Fishman et al. | |
| 5,145,565 A | 9/1992 | Kater et al. | |
| 5,152,775 A | 10/1992 | Ruppert | |
| 5,188,118 A | 2/1993 | Terwilliger | |
| 5,189,751 A | 3/1993 | Giuliani et al. | |
| 5,222,504 A | 6/1993 | Solomon | |
| 5,228,972 A | 7/1993 | Osaka et al. | |
| 5,279,294 A | 1/1994 | Anderson et al. | |
| 5,304,468 A | 4/1994 | Phillips et al. | |
| 5,307,263 A | 4/1994 | Brown | |
| 5,310,049 A * | 5/1994 | Bigelow et al. | 206/53 |
| 5,320,808 A | 6/1994 | Holen et al. | |
| 5,325,577 A * | 7/1994 | Bigelow et al. | 29/426.5 |
| 5,366,470 A | 11/1994 | Ramel | |
| 5,368,047 A | 11/1994 | Suzuki et al. | |
| 5,415,169 A | 5/1995 | Siczek et al. | |
| 5,418,142 A | 5/1995 | Kiser et al. | |
| 5,423,847 A | 6/1995 | Strong et al. | |
| 5,451,350 A | 9/1995 | Macho et al. | |
| 5,472,427 A | 12/1995 | Rammler | |
| 5,474,084 A | 12/1995 | Cunniff | |
| 5,514,152 A | 5/1996 | Smith | |
| 5,515,170 A | 5/1996 | Matzinger et al. | |
| 5,522,255 A | 6/1996 | Neel et al. | |
| 5,529,074 A | 6/1996 | Greenfield | |
| 5,567,617 A * | 10/1996 | Caprio et al. | 435/287.2 |
| 5,575,403 A | 11/1996 | Charlton et al. | |
| 5,580,794 A | 12/1996 | Allen | |
| 5,615,531 A * | 4/1997 | Nakai et al. | 53/136.4 |
| 5,630,986 A | 5/1997 | Charlton et al. | |
| 5,632,410 A | 5/1997 | Moulton et al. | |
| 5,686,829 A | 11/1997 | Girault | |
| 5,700,695 A | 12/1997 | Yassinzadeh et al. | |
| 5,714,390 A | 2/1998 | Hallowitz et al. | |
| 5,720,924 A | 2/1998 | Eikmeier et al. | |
| 5,738,244 A | 4/1998 | Charlton et al. | |
| RE35,803 E | 5/1998 | Lange et al. | |
| 5,758,643 A | 6/1998 | Wong et al. | |
| 5,776,157 A | 7/1998 | Thorne et al. | |
| 5,776,719 A | 7/1998 | Douglas et al. | |
| 5,788,651 A | 8/1998 | Weilandt | |
| 5,800,781 A | 9/1998 | Gavin et al. | |
| 5,801,057 A | 9/1998 | Smart et al. | |
| 5,810,199 A | 9/1998 | Charlton et al. | |
| 5,823,973 A | 10/1998 | Racchini et al. | |
| 5,824,491 A | 10/1998 | Priest et al. | |
| 5,830,219 A | 11/1998 | Bird et al. | |
| 5,846,490 A | 12/1998 | Yokota et al. | |
| 5,854,074 A | 12/1998 | Charlton et al. | |
| 5,855,801 A | 1/1999 | Lin et al. | |
| 5,857,983 A | 1/1999 | Douglas et al. | |
| 5,863,800 A | 1/1999 | Eikmeier et al. | |
| 5,871,494 A | 2/1999 | Simons et al. | |
| 5,879,311 A | 3/1999 | Duchon et al. | |
| 5,880,829 A | 3/1999 | Kauhaniemi et al. | |
| 5,885,211 A | 3/1999 | Eppstein et al. | |
| 5,891,053 A | 4/1999 | Sesekura | |
| 5,916,229 A | 6/1999 | Evans | |
| 5,935,075 A | 8/1999 | Casscells et al. | |
| 5,938,679 A | 8/1999 | Freeman et al. | |
| 5,951,492 A | 9/1999 | Douglas et al. | |
| 5,951,493 A | 9/1999 | Douglas et al. | |
| 5,951,582 A | 9/1999 | Thorne et al. | |
| 5,962,215 A | 10/1999 | Douglas et al. | |
| 5,964,718 A | 10/1999 | Duchon et al. | |
| 5,968,063 A | 10/1999 | Chu et al. | |
| 5,971,941 A | 10/1999 | Simons et al. | |
| 5,997,561 A | 12/1999 | Bocker et al. | |
| 6,022,324 A | 2/2000 | Skinner | |
| 6,027,459 A | 2/2000 | Shain et al. | |
| 6,036,924 A | 3/2000 | Simons et al. | |
| 6,048,352 A | 4/2000 | Douglas et al. | |
| 6,071,294 A | 6/2000 | Simons et al. | |
| 6,086,545 A | 7/2000 | Roe et al. | |
| 6,090,078 A | 7/2000 | Erskine | |
| 6,093,156 A | 7/2000 | Cunningham et al. | |
| 6,099,484 A | 8/2000 | Douglas et al. | |
| 6,117,630 A | 9/2000 | Reber et al. | |
| 6,120,462 A | 9/2000 | Hibner et al. | |
| 6,132,449 A | 10/2000 | Lum et al. | |
| 6,136,013 A | 10/2000 | Marshall et al. | |
| 6,139,562 A | 10/2000 | Mauze et al. | |
| 6,143,164 A | 11/2000 | Heller et al. | |
| 6,152,942 A | 11/2000 | Brenneman et al. | |
| 6,155,992 A | 12/2000 | Henning et al. | |
| 6,156,051 A | 12/2000 | Schraga | |
| 6,159,424 A | 12/2000 | Kauhaniemi et al. | |
| 6,171,325 B1 | 1/2001 | Mauze et al. | |
| 6,176,865 B1 | 1/2001 | Mauze et al. | |
| 6,183,489 B1 | 2/2001 | Douglas et al. | |
| 6,193,673 B1 | 2/2001 | Viola et al. | |
| 6,203,504 B1 | 3/2001 | Latterell et al. | |
| 6,206,841 B1 | 3/2001 | Cunningham et al. | |
| 6,210,420 B1 | 4/2001 | Mauze et al. | |
| 6,210,421 B1 | 4/2001 | Bocker et al. | |
| 6,228,100 B1 | 5/2001 | Schraga | |
| 6,231,531 B1 | 5/2001 | Lum et al. | |
| 6,261,241 B1 | 7/2001 | Burbank et al. | |
| 6,261,245 B1 | 7/2001 | Kawai et al. | |
| 6,283,926 B1 | 9/2001 | Cunningham et al. | |
| 6,285,454 B1 | 9/2001 | Douglas et al. | |
| 6,306,104 B1 | 10/2001 | Cunningham et al. | |
| 6,306,152 B1 | 10/2001 | Verdonk et al. | |
| 6,315,738 B1 | 11/2001 | Nishikawa et al. | |
| 6,319,210 B1 | 11/2001 | Douglas et al. | |
| 6,332,871 B1 | 12/2001 | Douglas et al. | |
| 6,352,514 B1 | 3/2002 | Douglas et al. | |
| 6,364,889 B1 | 4/2002 | Kheiri et al. | |

| | | |
|---|---|---|
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,595,451 B1 * | 7/2003 | Kang et al. ............ 242/381.2 |
| 6,789,329 B1 * | 9/2004 | Hester ..................... 33/760 |
| 7,056,475 B2 * | 6/2006 | Lum et al. ................. 422/100 |
| 7,337,072 B2 * | 2/2008 | Chen ........................ 702/19 |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0103499 A1 | 8/2002 | Perez et al. |
| 2002/0188224 A1 * | 12/2002 | Roe et al. .................. 600/584 |
| 2003/0088191 A1 | 5/2003 | Freeman et al. |
| 2003/0144608 A1 | 7/2003 | Kojima et al. |
| 2003/0153939 A1 | 8/2003 | Fritz et al. |
| 2003/0211619 A1 | 11/2003 | Olson et al. |
| 2003/0233112 A1 | 12/2003 | Alden et al. |
| 2003/0233113 A1 | 12/2003 | Alden et al. |
| 2004/0249311 A1 | 12/2004 | Haar et al. |
| 2007/0119710 A1 * | 5/2007 | Goldberger et al. .... 204/403.01 |

FOREIGN PATENT DOCUMENTS

| | | |
|---|---|---|
| DE | 42 34 553 A1 | 4/1993 |
| DE | 198 19 407 A1 | 11/1999 |
| DE | 198 49 539 A1 | 5/2000 |
| DE | 198 57 426 A1 | 6/2000 |
| DE | 101 05 549 A1 | 8/2002 |
| EP | 0 351 891 B1 | 1/1990 |
| EP | 0 299 517 B1 | 6/1993 |
| EP | 1 424 040 A1 | 6/2004 |
| JP | 04194660 A1 | 7/1992 |
| JP | 9-276235 | 10/1997 |
| JP | 2000116768 A2 | 4/2000 |
| WO | WO 93/02720 A1 | 2/1993 |
| WO | WO 93/12726 | 7/1993 |
| WO | WO 97/42888 | 11/1997 |
| WO | WO 99/39186 A1 | 8/1999 |
| WO | WO 01/00090 A1 | 1/2001 |
| WO | WO 01/08551 A2 | 2/2001 |
| WO | WO 01/34029 A1 | 5/2001 |
| WO | WO 01/66010 A1 | 9/2001 |
| WO | WO 02/056769 A1 | 7/2002 |
| WO | WO 02/100274 A1 | 12/2002 |
| WO | WO 2004/047642 A1 | 6/2004 |

* cited by examiner

BODY FLUID TESTING DEVICE

REFERENCE TO RELATED APPLICATIONS

The present application is a continuation of International Patent Application No. PCT/EP2003/014708 filed Dec. 22, 2003, which claims foreign priority to European Patent Application No. 02 028 894.0 filed Dec. 23, 2002, which are hereby incorporated by reference in their entirety.

BACKGROUND OF THE INVENTION

The present invention relates to body fluid testing devices and more specifically, but not exclusively, concerns a body fluid testing device that incorporates a test media cassette which contains test media used to test body fluid.

General Fluid Testing

The acquisition and testing of body fluids is useful for many purposes and continues to grow in importance for use in medical diagnosis and treatment and in other diverse applications. In the medical field, it is desirable for lay operators to perform tests routinely, quickly and reproducibly outside of a laboratory setting, with rapid results and a readout of the resulting test information. Testing can be performed on various body fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of body fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult, and is not advised for patients to perform on themselves.

Acquiring—Incising

The other common technique for collecting a body fluid sample is to form an incision in the skin to bring the fluid to the skin surface. A lancet, knife, or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe, and the like, may be useful for sampling and are less painful. However, they also produce lesser amounts of blood. These alternate sites therefore are generally appropriate for use only for test systems requiring relatively small amounts of fluid, or if steps are taken to facilitate the expression of the body fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek® Softclix lancet.

Expressing

Patients are frequently advised to urge fluid to the incision site, such as by applying pressure to the area surrounding the incision to milk or pump the fluid from the incision. Mechanical devices are also known to facilitate the expression of body fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of body fluid from an incision is the Amira AtLast blood glucose system.

Sampling

The acquisition of the produced body fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite, and Therasense FreeStyle test strips.

Testing General

The body fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the body fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise, and other factors. A proper control of the blood glucose level avoids hypoglycemia which may lead to insomnia and even sudden death as well as hyperglycemia resulting in long term disorders as blindness and amputations. Blood glucose is therefore a very important analyte to be monitored.

In testing for the presence of an analyte such as glucose in a body fluid, test systems are commonly used which take advantage of an oxidation/reduction reaction which occurs using an oxidase/peroxidase detection chemistry. The test reagent is exposed to a sample of the body fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing body fluids for properties on constituents.

Testing Media

As mentioned above, diabetics typically have to monitor their blood glucose levels throughout the day so as to ensure that their blood glucose remains within an acceptable range. Some types of sampling devices require the use of testing strips that contain media for absorbing and/or testing the body fluid, such as blood. After testing, the testing media contaminated with blood can be considered a biohazard and needs to be readily disposed in order to avoid other individuals from being exposed to the contaminated test strip. This can be especially inconvenient when the person is away from home, such as at a restaurant. Moreover, individual test elements can become easily mixed with other test strips having different expiration dates. The use of expired test elements may create false readings, which can result in improper treatment of the patient, such as improper insulin dosages for diabetics.

Test Media Cassettes

Analytical systems with test media cassettes which allow multiple testing have been described in the prior art. There are available dispensers which contain a limited number of test elements; as for example, 1 to 2 dozen strips which are individually sealed. Blood glucose meter using such a test strip dispenser are in the market under the names AccuChek Compact (Roche Diagnostics GmbH) and DEX (Bayer Corporation). Consumers, however, demand systems that contain even more strips to reduce loading actions to be performed by the user. A suitable way to package a higher number of test elements are test films as e.g., described in U.S. Pat. No. 4,218,421 and U.S. Pat. No. 5,077,010. These test systems are, however, designed to be used in the environment of automated laboratory systems and are therefore not suited for patient self testing. DE 198 19 407 describes a test element cassette employing a test media tape for use in the patient self testing environment. A number of practical problems are, however, still unsolved when relying on the device described in DE 198 19 407. Test media used for blood glucose testing as well as for other analytes are prone to deterioration by humidity from the environmental air. It is therefore a serious problem to keep unused test media free from humidity to avoid deterioration which would lead to incorrect analytical results. U.S. Pat. No. 5,077,010 discloses containers for test media tape which have an outlet for the tape which is sealed by a blocking member or a resilient member (see in particular FIGS. 21 to 33 and corresponding disclosure). This way of sealing is comparable to the type of sealing known from photographic film boxes. The automated analytical instruments of U.S. Pat. No. 5,077,010 have a high throughput and therefore the required onboard stability is short (typically one or two days only). Contrary to that, the required onboard stability in the home diagnostic market is much longer. Considering a patient doing two testings a day and a test media capacity of a cassette in the range of 100, stability of the test media cassette after insertion into a meter (i.e. the onboard stability) needs to be in the range of 50 days. The situation, however, may be even worse considering that the patient may have a second meter and uses the present meter only from time to time. In the field of blood glucose testing, onboard stability therefore has to be shown for at least three months. It has been shown that the type of sealing as disclosed in U.S. Pat. No. 5,077,010 is insufficient to achieve the onboard stability as required in the home monitoring environment.

It is an aim of the present invention to propose body fluid testing devices and test media cassettes which contain a larger number of test media than the body fluid testing systems currently on the market and which guarantee long onboard stability of the test media. Further, it is an aim to propose meters for multiple testing which are easy to operate and which have a handheld size.

SUMMARY OF THE INVENTION

According to the present invention, it was found that the concept of test tape meters can be highly improved. A test media tape is employed on which the individual test media are spaced one from the other so that free tape portions are located between successive test media. Such a test media tape is contained in a supply container which shelters the test media tape against humidity. Test media can be taken out of the container via an opening by using the tape as a transporting means. The test media which are still located within the supply container are protected against humidity by using a sealing means for sealing the opening of the container while a free tape portion is located between the sealing means and a surface of the supply container. This type of sealing enables very practical testing devices which can provide numerous test media without the need for the user to load the testing device with separate individual test elements.

Due to the spacing of the test media, the material of the free tape portion can be chosen mostly independent from the test media material to achieve a proper sealing with the described sealing means. It has been shown that tape materials as e.g., plastics for audio cassettes are well suited for this purpose. Suitable tape materials are plastic foils from polyester, polycarbonate, cellulose derivatives, and polystyrene. It is, however, preferred to choose non-hygroscopic materials which do not transport water or water vapour to a high degree. According to this, tapes without free tape sections between successive test media cannot be sealed properly since the test media material is porous and thus would allow humidity to flow into the supply container even when the tape is sealed according to the present invention. Further, the thickness of the tape in the free tape portion is an important parameter to control proper sealing. It has been shown by the inventors of the present invention that leakage of humidity into the storage housing decreases with decreasing tape thickness. While there are a number of interacting parameters, the particular effect of the tape thickness can be seen from FIG. 1. The tape (T) is located between a sealing means (S) having a deformable gasket (G) and a surface of the container housing (H). The sealing means applies pressure in the direction of the housing, thus pressing the gasket onto the tape and housing surface. The gasket is stronger compressed in the region of the tape as it is right and left from the tape. The leakage regions (L) which are not filled by tape or gasket material allow influx of humid air. Decreasing the tape thickness hence reduces the cross section of the leakage regions. It has been shown that a tape having a thickness below 100 micrometers is well suited to limit humidity influx into the housing even if the gasket is relatively rigid. Even more preferred are tape thicknesses below 50 micrometers.

The sealing means is a means that closes the opening of the housing (container) in which uncontaminated test media tape is stored. The sealing means preferably is a body from a gasket material or a body of a material to which a gasket is fixed. Alternatively, the gasket may be fixed to the surface onto which the sealing means presses to close the container opening. Also embodiments are possible where gasket material is present on the surface as well on the body of the sealing means.

Further, it can be understood with view to FIG. 1 that an increasing flexibility of the gasket reduces humidity influx. It has shown that gaskets with a shore hardness (A) of less than 70, preferably in a range of 30 to 50 are well suited. The shore hardness (A) is defined by DIN 53505 (June 1987). Gasket materials which are well suited to practice the present invention are thermoplastic elastomers. Especially suited are such elastomeres which comprise polystyrene as the hard component and polymerisates of butadiene or isoprene as the soft component. Suitable gasket materials can be obtained under the tradenames Kraton D, Kraton G and Cariflex TR from Shell and Solprene from Philips.

Gaskets are referred which have an annular shape such that they annularly surround the container opening. It has been found that with such annular gaskets, proper sealing can be achieved, while sealing with non-annular gaskets (e.g., straight-line shaped gaskets), proper sealing is much harder to achieve since it is harder to close the leakage at the ends of such gaskets.

The body of the sealing means as well as the body of the storage container should be made from materials which are mostly impermeable to humidity. This can be achieved by numerous materials. Due to production aspects, plastics such as polypropylene, polyethylene, and polystyrene are, however, preferred. The materials, however, do not need to be totally impermeable to humidity since it is possible to capture humidity which has diffused in by drying agents.

The sealing means further comprises a pressure means that serves to apply pressure to the sealing means body so as to achieve the sealing. Such pressure means are e.g., coil springs, pneumatic actuators, motors, electromagnets, compressed materials, or stressed materials. From the preferred embodiments, it will become clear that in particular elastic sealing means which in their rest position press onto the sealing means body are easy and cheap to manufacture.

The pressure necessary for proper sealing largely depends on the shore hardness of the employed gasket as well as the area to be sealed. The required pressure, however, typically is in the range of a few Newton or below.

Further optional measures to increase onboard stability of the test media will be described later on in connection with the specific embodiments.

A first general concept of the present invention concerns a body fluid testing device that incorporates a test media tape. The test media tape holds test media that are used to collect body fluid samples which are analyzed with a sensor. Advantageously the test media tape is housed in a cassette so that after the test media of a cassette are used up, a fresh test media cassette can be inserted into the testing device. The test media tape is indexed before or after each test so that successive tests can be performed without requiring disposal of the used test media. The test media can be indexed manually or automatically.

The test medium is a medium which contains a test chemistry that with analyte from a sample leads to detectable results. For further details of test chemistry and testing, see section "Testing General". Preferably, the test media are designed to soak up the test fluid sample. This prevents the testing device from becoming contaminated by the body fluid sample. As will be described in more detail later on, it is preferred to employ a test media tape which comprises a tape on which test media are arranged with free tape regions between successive test media. The preferred arrangement therefore has a structure with regions as follows: tape with test medium—tape without test medium—tape with test medium—and so on. The tape can be made e.g., from conventional plastic tape as used for audio cassettes. The test media are attached to the tape, e.g., by gluing, welding, or by use of an adhesive tape.

In accordance with one aspect of the present invention, there is provided a body fluid testing device for analyzing a body fluid. The testing device includes a test media cassette that includes a test media tape adapted to collect the body fluid. The cassette includes a supply portion that stores an uncontaminated section of the test media tape. A storage portion for storing a contaminated section of the test media tape may be further employed. Contrary to the supply portion which is designed to shelter the test media tape from humidity from the surrounding environment, it is preferred to design the storage section for contaminated tape to be open to some extent so that the test media which are soaked with sample can dry out. Such an open design may be realized by a plastic container having slits or recesses for gas exchange with the surrounding environment.

An important measure which advantageously can be used with embodiments of the present invention is a drying material within the test media tape supply container. Humidity which has entered the container by diffusion through wall materials or during an opening cycle is absorbed and cannot deteriorate test media. The sealing concepts of the present invention are, however, not obsolete due to the use of drying material since the amount of humidity entering without sealing means during the onboard time would be much too high to be cared for by rational amounts of drying material. Suitable drying materials are well known in this field of art, these are e.g., molecular sieves, silica gel, etc.

The present invention further proposes one-way devices where the test media tape belongs to the testing device so that the whole device is discarded when the test media tape is used up. Alternatively the test media tape may be arranged in a disposable cassette which is removably received in the testing device.

The term "body fluid testing device" will be used for both embodiments (e.g., with and without cassette) within this patent application. However, when embodiments employing a test media cassette are concerned the term will also be used to designate the device into which the cassette is inserted.

As described in European Patent Application No. 02026242.4 (European Publication No. EP 1 424 040 A1), which is hereby incorporated by reference in its entirety, the test media tape onto which body fluid will be applied advantageously can be exposed in a tip-like shape to simplify body fluid application to a test medium. For this purpose the test media tape can be guided over a convex tip portion which may belong to the testing device or to the test media cassette.

The testing device further may comprise a pricking unit for pricking a body portion. The lancing opening of that pricking unit advantageously can be arranged in or close to the convex portion so that the tip portion (if present) can be used for convenient pricking as well. The pricking unit may be arranged below the test media tape and a lancing device can either penetrate the test media tape or can extend through a recess in the test media tape.

The testing device further may employ visual user guidance for application of body fluid samples. According to this embodiment, the testing device comprises an illumination unit which indicates by illumination a portion of a test element where body fluid has to be applied. The illumination serves for a timely and/or spatial guidance of the user to apply body fluid. Further the illumination may serve to indicate the location where to position a body portion for pricking. An illuminated area on the test medium may further indicate the amount (or the droplet size) of body fluid which is required by the testing device.

Another aspect of the present invention concerns a test cassette for collecting a body fluid sample. The cassette includes a housing that has a supply portion in which uncontaminated test media tape is enclosed. The housing further includes a storage portion in which a contaminated section of the test media tape is enclosed after contamination. For sealing unused test media against humidity, a tape is employed which has free tape portions between successive test media as already described above such that the sealing concept of the present invention can be employed. The sealing means of the present invention may belong to the test media cassette or to the testing device. Further embodiments are possible where parts of the sealing means, as e.g., a pressure application plate, belong to the testing device while other parts, as e.g., a gasket, belong to the cassette. Advantageously the container which houses the uncontaminated test media tape is closed against humidity with the exception of the opening which can be closed by the sealing means.

The cassette further may include a convex tip portion over which the test media tape runs and at which the test media tape is exposed to the body fluid.

In a particular embodiment, a supply reel is disposed in the supply portion of the housing around which the uncontaminated section of the test media tape is wrapped, and a storage reel is disposed in the storage portion of the housing around which the contaminated section of the test media tape can be wrapped. In embodiments which employ a reel for storing uncontaminated test media tape, it is preferred that the axis of this supply reel does not penetrate the supply container housing to avoid the leakage of humid air into the container.

Most test media are destroyed or altered by humidity, sunlight, etc. Therefore measures have to be taken to shelter the test media before they are used onboard of a testing device. A first measure is to package the whole test media cassette before use such that contact with humidity from the surrounding is prevented. This can be achieved by e.g., a blister package. Alternatively the cassette housing can be made being closed against humidity with the exception of the region where test media are exposed for body fluid application. Embodiments can be contemplated which employ a humidity proof cover over the exposure region which can be removed prior to use of the cassette.

Further this invention concerns a method of using a testing device comprising the steps of:
  providing a supply portion comprising a container in which uncontaminated test media tape is contained, said container further having an opening for withdrawing test media tape from the container,
  providing a sealing means which can close said opening against the surrounding,
  actuating the sealing means to open said opening of the container, and
  removing a portion of test media tape from the container to expose an unused test medium.

The method further may include the steps of:
  actuating the sealing means to close said opening of the container, and testing.

Actuation preferably means pressing the sealing means onto a surface of the supply portion container.

A further step may be included in the above method which concerns a pricking for generating a body opening prior to testing.

It is preferred when the closing means can assume two distinct positions.

In a first, closed position the sealing means sealingly engages a surface of the supply container so as to close it and to shelter test media within it against humidity.

In a second, open position the sealing means is opened to allow test media tape to leave the supply container. The opening has to be wide enough to allow test media tape portions with test media (which are normally thicker than the tape alone) to pass through.

A method for providing test media therefore may comprise the steps of:
  providing a supply container in which uncontaminated test media tape is contained, said container further having an opening for withdrawing test media tape from the container,
  providing a sealing means which closes said opening against the surrounding,
  moving the sealing means from a first, closed position into a second, open position to open said opening of the container,
  removing a portion of test media tape from the container to expose an unused test medium, and
  moving the sealing means from said second, open position to said first, closed position to close said opening of the container.

Again it has to be understood that, when the sealing means is closed, a free tape portion is located between the sealing means and a surface on which the tape is resting. Said surface is typically a surface of the supply container.

The closing via the sealing means preferably means that the sealing means is pressed onto another surface (typically a container surface) to generate a sealing of the uncontaminated test media tape against humidity.

Other forms, embodiments, objects, features, advantages, benefits, and aspects of the present invention shall become apparent from the detailed drawings and description contained herein.

SHORT DESCRIPTION OF THE FIGURES

Figure 2:
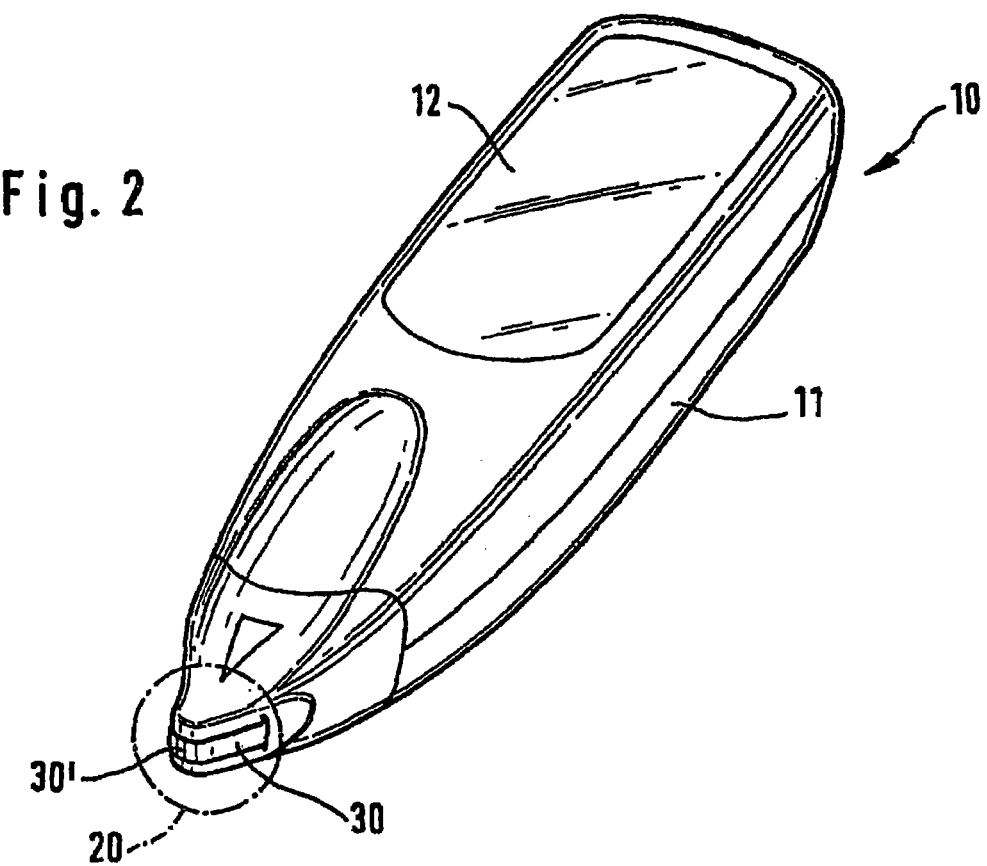

FIG. 1: Schematic drawing showing leakage regions.
FIG. 2: Perspective view of a testing device.

Figure 3:
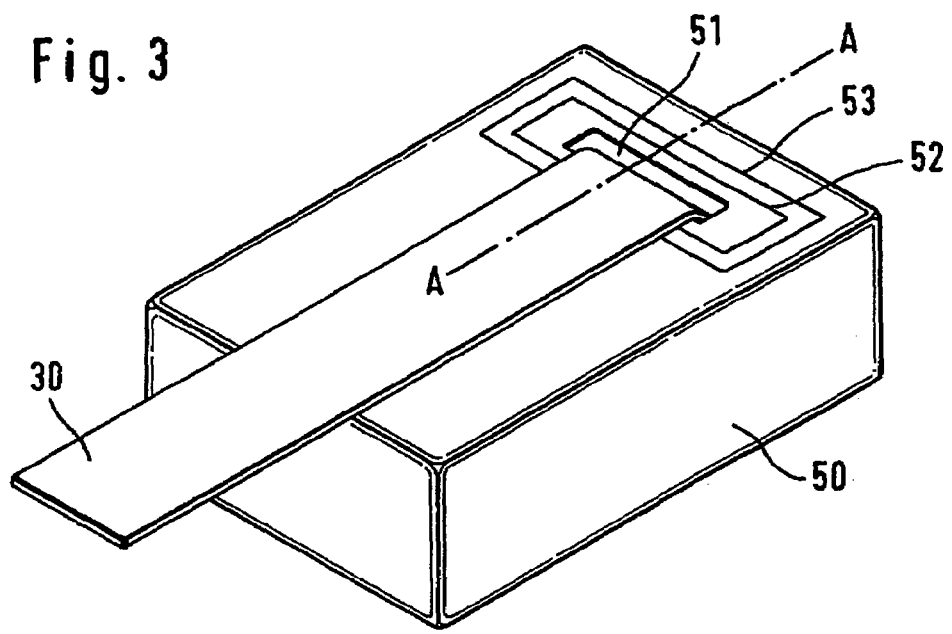
Figure 4:
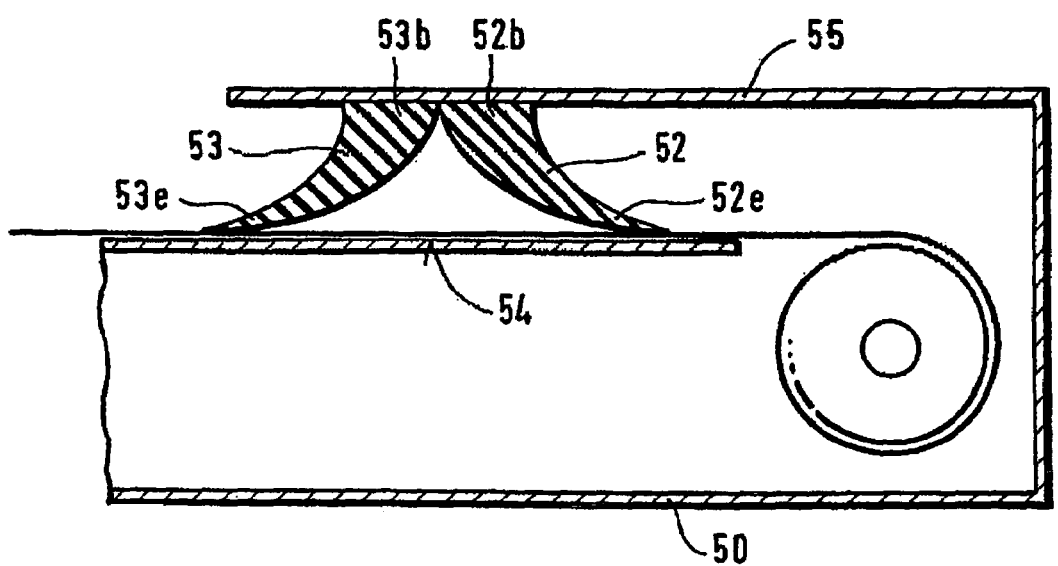
Figure 5:
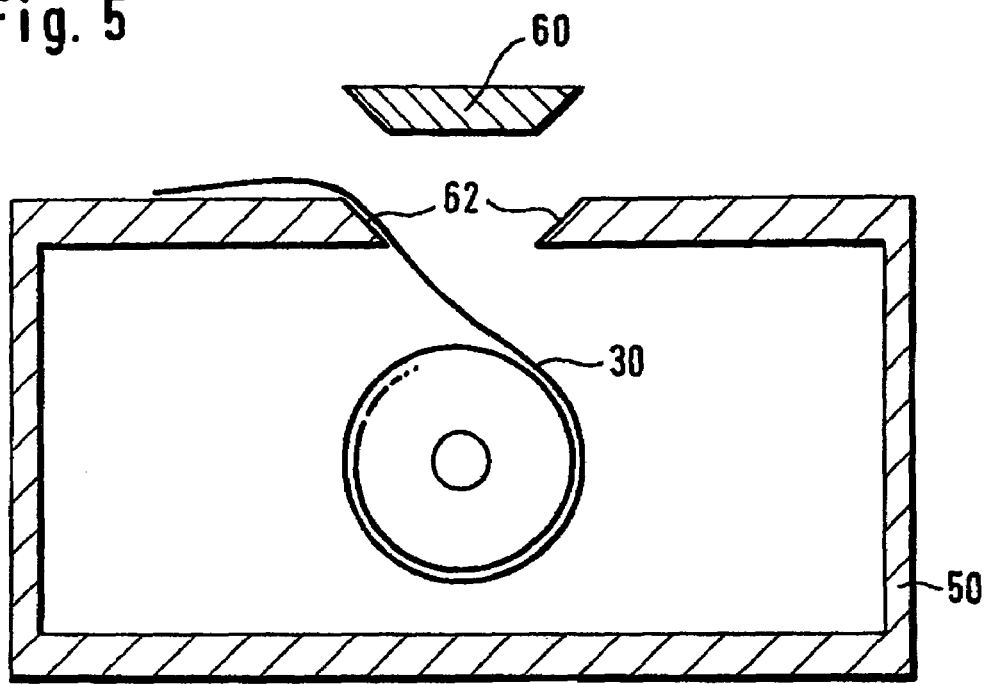
Figure 6:
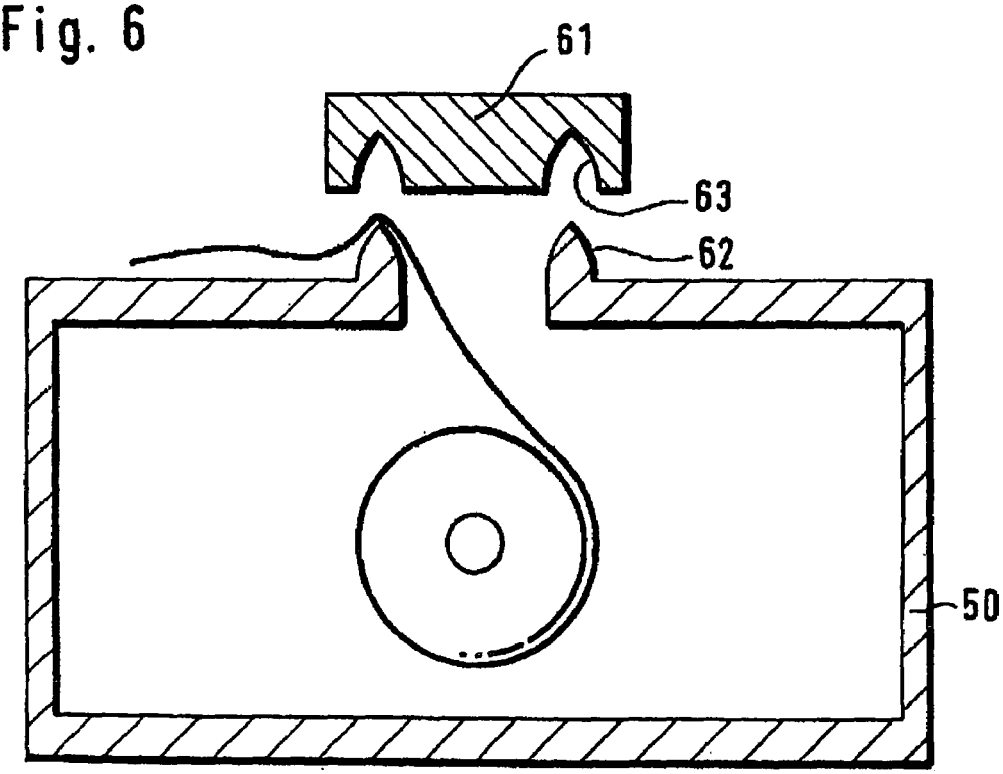
Figure 7:
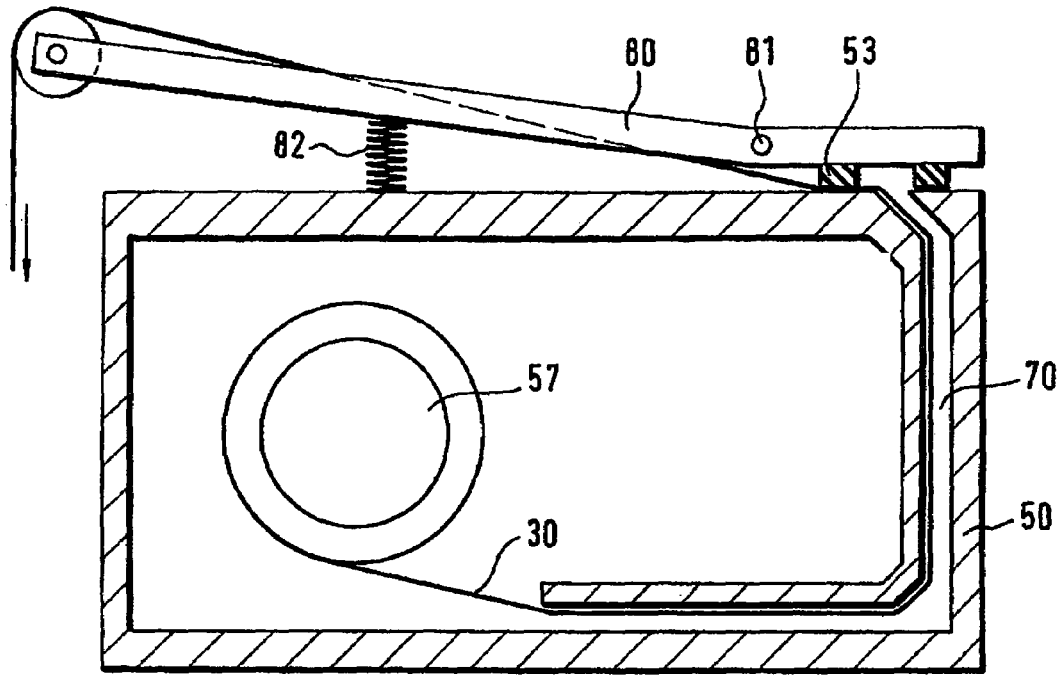
Figure 8:
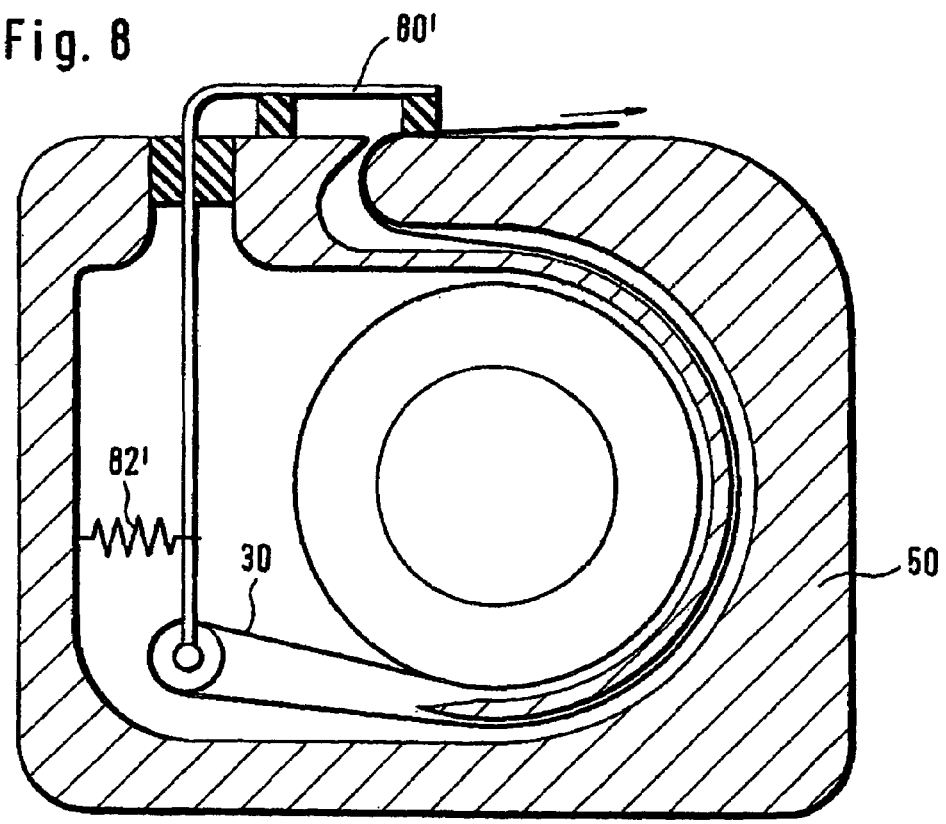
Figure 10:
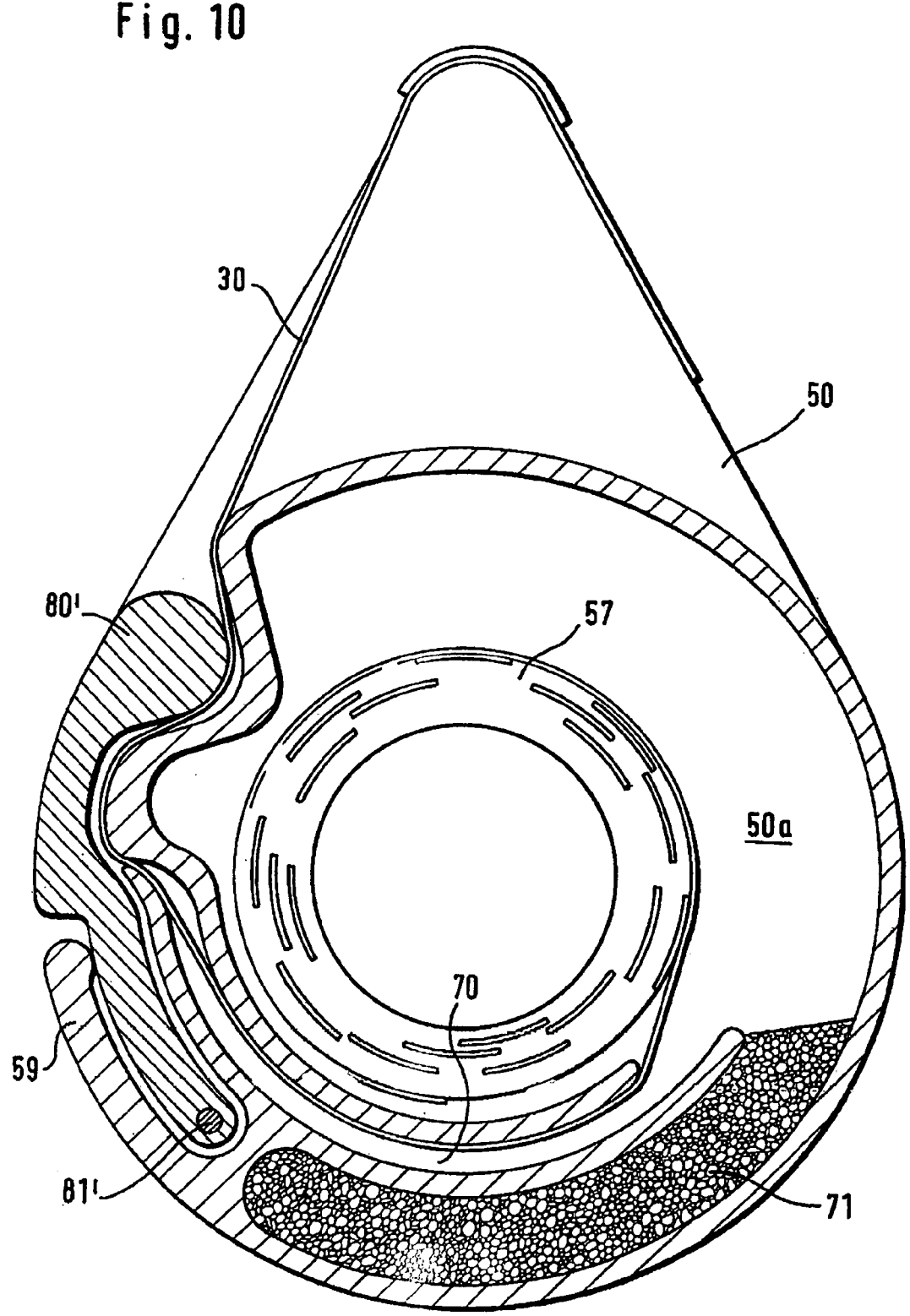
Figure 11:
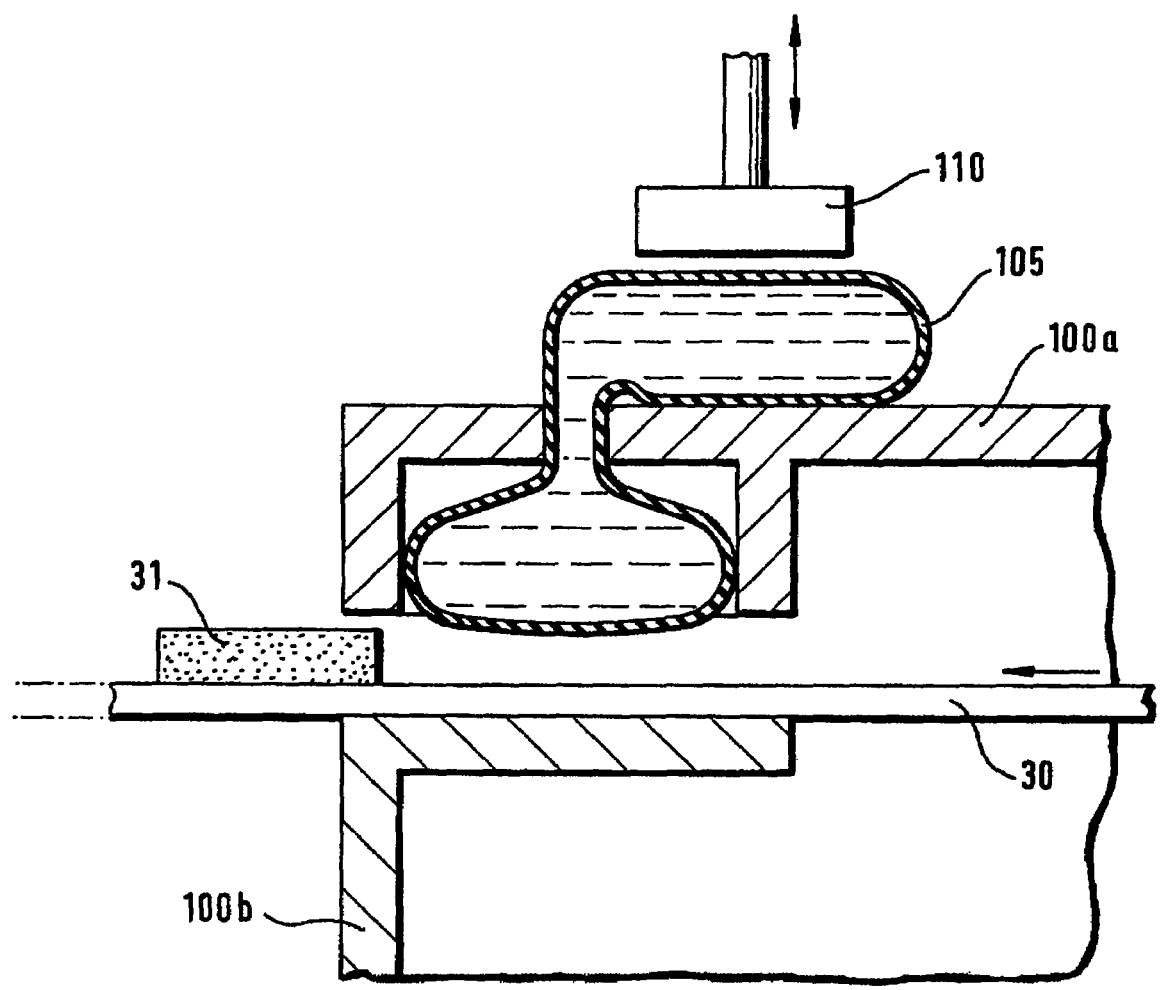

FIG. 3: Perspective view of a sealing concept.
FIG. 4: A cross-sectional view along line A-A of FIG. 3.
FIG. 5: Test media cassette with trapezoidal sealing means.
FIG. 6: Test media cassette with form fitting sealing means.
FIG. 7: Test media cassette having a lever for opening the supply container by tensioning test media tape.
FIG. 8: Test media cassette having a lever for opening the supply container by tensioning test media tape.
FIGS. 9A, 9B, 9C, and 9D: Testing device during various stages of operation.
FIG. 10: Testing magazine with self-sealing sealing means.
FIG. 11: Hydraulic sealing means.

DESCRIPTION OF SELECTED EMBODIMENTS

For the purposes of promoting and understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It will be apparent to those skilled in the art that some of the features which are not relevant to the invention may not be shown for the sake of clarity.

The humidity sealing principle is shown in FIG. 1. On the housing surface (H) which preferably has a low roughness the test-carrier-tape (T) is pressed by the sealing material (G). The sealing force (F) presses the flexible gasket around the test media tape. The remaining leakage channels (L) are minimized by selection of Gasket material, tape thickness, sealing force and the time pattern in which the sealing means is being moved.

A body fluid testing device (10) is shown in FIG. 2. The drawing of the device shows a housing (11) and a display (12) for displaying test results as well as instructions of use. At the front end of the device there can be seen a tip portion (20) over which the test media tape (30) runs. A test medium at the front end of the testing device is exposed by the tip portion in a tip like manner which facilitates the application of body fluid. The tip portion for this reason at least partially projects out of the contour of the housing (11) of the testing device to be accessible for a body portion (e.g., finger or arm). At the tip portion there can be seen an illuminated area (30') which indicates the position for sample application.

FIG. 3 shows an improved embodiment of the sealing concept of the present invention. A portion of the test media tape (30) is located outside the housing (50) of the supply portion. The housing has an opening (51) via which tape can be taken out. The squares (52, 53) depicted on the housing show the locations on the housing surface onto which gaskets of the sealing means (not shown) press during sealing of the opening. Using two (or more) gaskets for sealing improves leakage protection. It is preferred to employ annular gaskets as shown, which annularly presses onto a region around the opening (51) to include the opening within the cross-sectional area of the annular gaskets. When two or more annular gaskets are employed, it is preferred when an annulary gasket fully includes the next smaller annular gasket.

In FIG. 4 there is depicted a cross-sectional view of FIG. 3 taken along line A-A. FIG. 4 only shows the portion of FIG. 3 which is left to the container opening as well as the opening. It can be seen that the gaskets are not aligned vertical to the surface of the housing (50) but that they are inclined or angled relative to vertical. The exterior gasket (53) in direction from its base portion (53b) to its free end (53e) is inclined away from the opening (51). The interior gasket (52) is inclined in direction from its base portion (52b) to its end portion (52e) towards the opening. Inclination of the exterior gasket serves to block incoming air more efficiently as a gasket without such inclination would achieve. Due to the inclination the sealing is strengthened when air tries to enter the housing (this is the case when the pressure inside the housing is lower than the outside pressure) since the air pressure increases the pressure of the end portion (53e) of the gasket onto the surface (54) of the container (50). The same principle applies to the interior gasket for the inverse case when the pressure inside the housing is higher than the outside pressure.

As can be further seen in FIG. 4 it is advantageous when the gaskets taper from their base portion towards their free end portion. The smaller the gasket at the end portion, the more flexible it is to match with the shape of the tape thus reducing the cross section of the leakage areas. The smaller the area covered by the annular gasket around said opening (51), the lower the required force to achieve a small leakage channel (L).

In this embodiment the pressure means (55) has the shape of a plate to whose underside the gaskets are fixed. It is particularly preferred to fix the gaskets to the plate by two component molding of plate and gasket. A spring means (not shown) for applying pressure to the pressure plate (55) belongs to the testing device.

Further in FIG. 4 there can be seen that the test media tape does not necessarily need to be wrapped on a reel. The arrangement of the tape within the storage container is more or less arbitrary but needs to avoid jams or blockage.

FIG. 5 shows a cross-sectional view of an embodiment having a trapezoidal sealing means (60) which presses onto an inclined surface (62) of the supply container (50). The sealing means itself can be made from a sealing material (e.g., rubber gum) or a sealing material (gasket) can be present on the surface of the sealing means which presses onto the surface of the supply container. Sealing in this embodiment again is made when a free tape portion is located in the region where the sealing means presses against the test media tape. The angle shown in FIG. 5 preferably is in the range from 0 to 45 degree.

FIG. 6 is a similar embodiment as shown in FIG. 5. Instead of a trapezoid sealing means, a form fitting sealing means (61) is employed. The surface of the housing (50) has a contour (62) at the opening which fits to a contour (63) of the sealing means (61). The contours of the sealing means can be made from a material functioning as a gasket itself (e.g., rubber gum) or a gasket can be present on the surface of the sealing means. However, even the inverse sealing principle with a gasket fixed on the surface of the housing can be employed.

FIG. 7 shows a cross-sectional view of a test media tape container (50) having a sealing means. The test media tape (30) is wrapped on a reel (57). From the reel the tape is guided through a diffusion channel (70) and leaves the container via the opening of the container. In rest the opening is sealed by an annular gasket (53) which is fixed to a first arm of a lever (80). Such levers are also known as a "dancer" in the art. The lever has a center of rotation (81). A spring element (82) keeps the gasket pressed onto the container surface. The test media tape (30) is located between gasket and container surface in the way already described (i.e. a free tape portion is located between gasket and container surface). The tape located outside the container is guided over a wheel at the other arm of the lever. When tape is drawn in the direction as shown in FIG. 7 the tape tension rotates the lever (80) against the spring force (82) around (81). This movement reduces the contact pressure of the gasket (53). The tape starts slipping through the gasket. Thus the tape section inside the housing gets tensioned. On further movement the friction of the reel increases the tape tension and thus causes a larger lift of the gasket. The opening created is large enough to leave through a test medium without touching the gasket. The tape now can be drawn out of the container. When a sufficient tape portion has been taken out of the container, the testing device (or a user) stops tearing the tape and the sealing is closed due to a movement of the lever caused by the spring element. In this embodiment it is advantageous when the reel (57) is friction loaded since the force acting on the lever is created by retention of the tape. In other embodiments a friction loading of the supply reel is also advantageous since it may avoid uncontrolled winding-up of the tape which can lead to jamming. Furthermore a tape properly wound on a reel has the advantage that test media underneath the outermost tape layer are shielded against humidity which already may have entered the housing.

A further important (but optional) measure to keep humidity away from unused test media is the diffusion channel (70) of FIG. 7. This channel serves to decrease the convectional exchange of air between the interior of the container and the surrounding environment during opening of the sealing. The channel limits the air exchange at the opening and thus the amount of humidity intake during the time of taking out a new test medium from the container. The humidity in the channel decreases along the way from the opening to the reel. The prevention of convection by the channel limits the intake of humidity into the container to diffusion which is a much slower material transport than convection.

FIG. 8 shows a further embodiment of a self sealing test media cassette. Self sealing in this context means that the cassette itself closes its opening without the need for forces from the outside acting on it to close its sealing. The cassette further opens the sealing on tensioning of the test media tape which is a preferred embodiment. The lever (80') of this embodiment has a first lever arm mostly inside the test media supply container (50). As in the foregoing figure the test media tape (30) is guided over a roller at one arm of the lever while the other arm of the lever holds an annular sealing gasket for sealing the container opening. When the test media tape is tensioned the lever is actuated and opens the sealing to free the tape so that a fresh portion of test media tape with an unused test medium can be taken out. After this the tension force applied to the tape can be reduced and the lever rotates driven by the spring means (82') of the cassette to close the container opening.

FIGS. 9A, 9B, 9C, and 9D shows a testing device (10) with a test media cassette (50) inserted into it as well as steps of using this device.

Figure 9A:
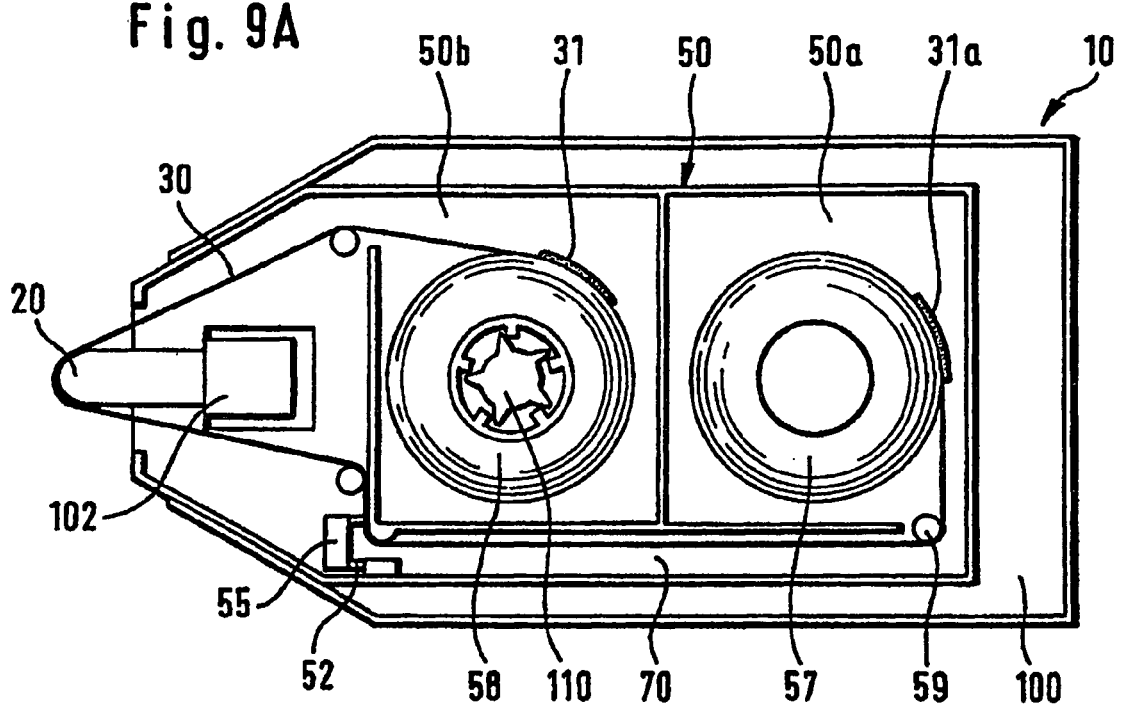

As can be seen from FIG. 9A, the testing device comprises a housing (100) in which the cassette is received. The cassette has a supply portion (50a) containing a supply reel (57) onto which uncontaminated test media tape (30) is wrapped. FIG. 9 depicts the test media portions (31) as pads which are fixed to a tape. The test pads are fixed to the tape via a double sided adhesive tape. Production of the test media tape therefore can easily be achieved by first removing a protection foil from a first side of an double side adhesive, applying a test medium pad to it and then removing a protection foil from a second side of the double sided adhesive and applying the compound structure of test medium pad and adhesive to the tape. This process can be easily automated. Alternatively, a double sided adhesive can first be applied to the tape and then applying a test medium pad to the adhesive. Other production methods, such as gluing test media to the tape, are possible as well.

Used (contaminated) test media tape is wrapped onto a storage reel (58) in the storage section of the test media cassette. Transport of the test media tape is made by a motor (110) of the testing device (10) which has a gear wheel for engaging with the gears of the storage reel and to rotate the storage reel. It is normally sufficient to employ only a single motor for winding the storage reel in a direction to move tape from the supply reel to the storage reel. For proper positioning of test media for sampling and/or testing it may be advantageous to move the tape in inverse direction as described before. This may be achieved by a separate motor winding the supply reel or a mechanics allowing a movement of the supply reel with the motor for rotating the storage reel. Further it is possible to employ a spring mechanically coupled to a friction loading means which is coupled to the supply reel. When tape is withdrawn from the supply reel by winding tape onto the storage reel the spring is loaded and the spring tension may be used to move back the tape a bit. This can be achieved by rotating back the motor and the supply reel will also rotate back caused by the spring tension so that the tape is still held under a sufficient stress to press it onto the tip for proper detection as well as to avoid jams caused by loose tape. By such a mechanism it is possible to properly position a test medium e.g., on the tip (20) when it has been moved too far at first.

However, it is preferred to avoid such a process by positioning of the test media by proper movement in one direction (the transport direction) only. Positioning of the test media on the tip may be achieved by the same optics as employed for reading the test media. It is, however, also possible to employ a separate position detection means which preferably operates optically. Detection of proper positioning can be achieved by employing test media and tape of different reflectance so that a reflectance monitoring during tape transport indicates by a change in reflectance when a test medium comes into reading position. However, it may also be advantageous to employ indication marks—as e.g., black bars—to the tape which are detected optically when they are detected by the positioning detection means.

The testing device further comprises a control unit which controls the steps of tape transport, opening and closing of the sealing, and reading of test media. The control unit or a separate calculation unit is further employed for calculation of analytical results from the obtained readings. The position detection means may also be controlled by the control unit.

The cassette further comprises a tip (20) over which the tape is guided. This (optional) tip serves for a convenient sample application by e.g., the finger tip. For more details of the tip and how the tape is prevented from falling off the tip reference is made to the copending European Patent Application No. 02026242.4, which is hereby incorporated by reference in its entirety. The cassette further has a recess for receiving a metering optics (102) belonging to the testing device. The part of the optics visible in FIG. 9A is a light coupling element for coupling light into the tip (20) to illuminate a test medium located on the tip. When sample is applied to this test medium the intensity of light reflected back from the underside of the test medium changes and the reflection intensity (preferably at a particular wavelength) can be read by a detector (not shown) and the intensity can be converted by the control unit or a calculation unit into an analytical concentration. With the aim to get optical readings from the test medium, it is either preferred to employ a tape material which is mostly transparent for the light to be detected or to employ a tape with a recess below the test medium as known from optical test elements as e.g., sold under the brand name Glucotrend.

(Departing from the embodiment shown in FIG. 9A it is, however, also possible to employ test media which operate as known from electrochemical test elements. In such embodiments the testing device contacts the test medium in use with electrodes and employs a test device controlling the application and measurement of current or power to obtain readings which can be converted into analyte concentrations.) Optical as well as electrochemical concentration measurement with disposable test elements is, however, well known in the art and therefore will not be described in more detail.

FIG. 9A shows the testing device (could also be called a testing system since the testing device houses a test media cassette) in its storage position with the sealing (52, 55) closed. The testing device comprises a pressure actuator (e.g., a coil spring) which presses the sealing plate (55) having an annular gasket (52) at the side facing away from the actuator onto an opening of the cassette (50). It can be seen that a free tape portion is located between the opening of the cassette and the gasket when the sealing is closed. This embodiment has a diffusion channel (70) connecting the opening with the supply section in which the uncontaminated test media tape is contained. It can be further seen that the supply section (50a) is closed against the surrounding when the sealing is closed, while the storage section (50b) is partially open to the surrounding. The test media cassette further has rollers or pins (59) over which the tape is guided.

Figure 9B:
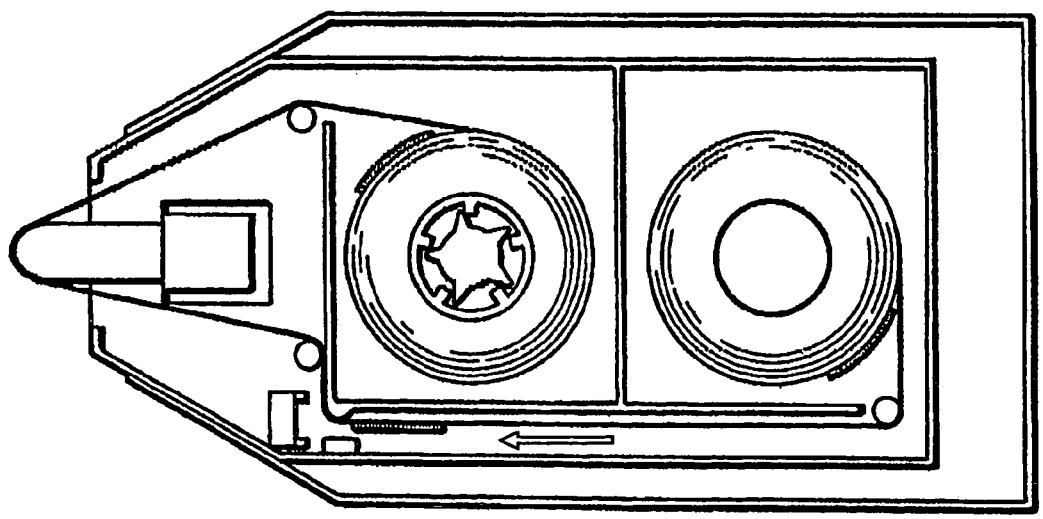

FIG. 9B shows the testing device with the sealing opened. Opening can be achieved by moving the pressure plate (55) away from the opening against the force of the pressure actuator. This can be done by a reverse attractor which withdraws the pressure plate from the opening (e.g., an electromagnet which attracts the pressure plate). FIG. 9B also shows that the test medium (31a) has been moved from a position on the supply reel (see FIG. 9A) into a position within the diffusion channel but still located within the supply section. It has to be understood that FIG. 9B is a snapshot of in between a test medium transport phase. The depicted position of the test medium is no typical waiting position but a position to last only shortly to keep the time period of opening the sealing as short as possible. The arrow shows the direction of tape transport.

Figure 9C:
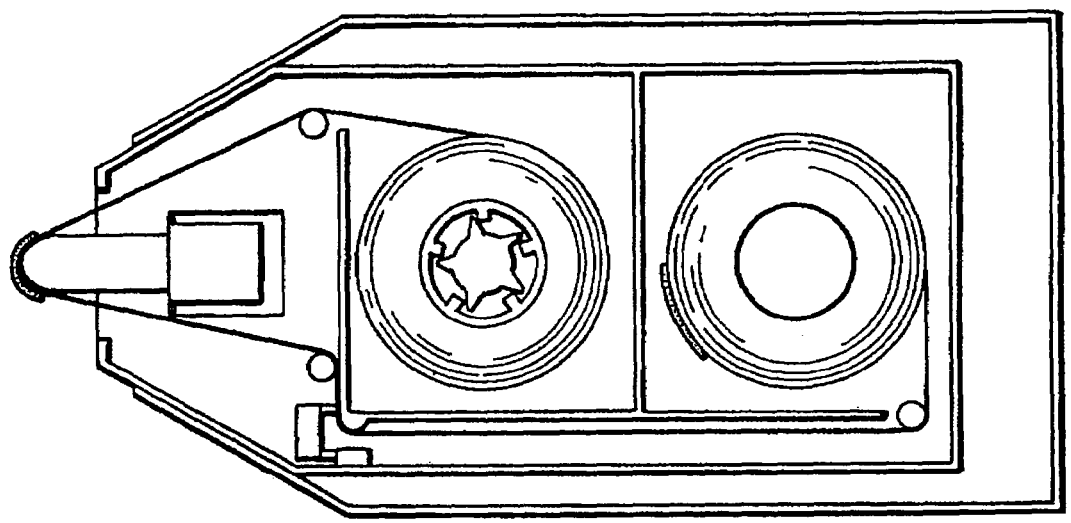

In FIG. 9C the sampling position for sampling body fluid can be seen. The test medium (31a) is located on the tip and the sealing is again closed. After body fluid application to the test medium on the tip, the testing device reads light reflected from the underside of the test medium to obtain a reading which can be converted into analyte concentration. It has to be understood that it is preferred if the body fluid application and reading are conducted in the same tape position so that no additional tape transport requiring opening of the sealing is necessary. However, it may also be advantageous to employ a reading position which is apart from the sampling position since this enables a reading optic or electrochemical analysis unit within the testing device at a different place. The closed sealing of FIG. 9C can be obtained by deactivating the reverse actuator so that the pressure actuator again presses the pressure plate onto the opening of the supply section.

Figure 9D:
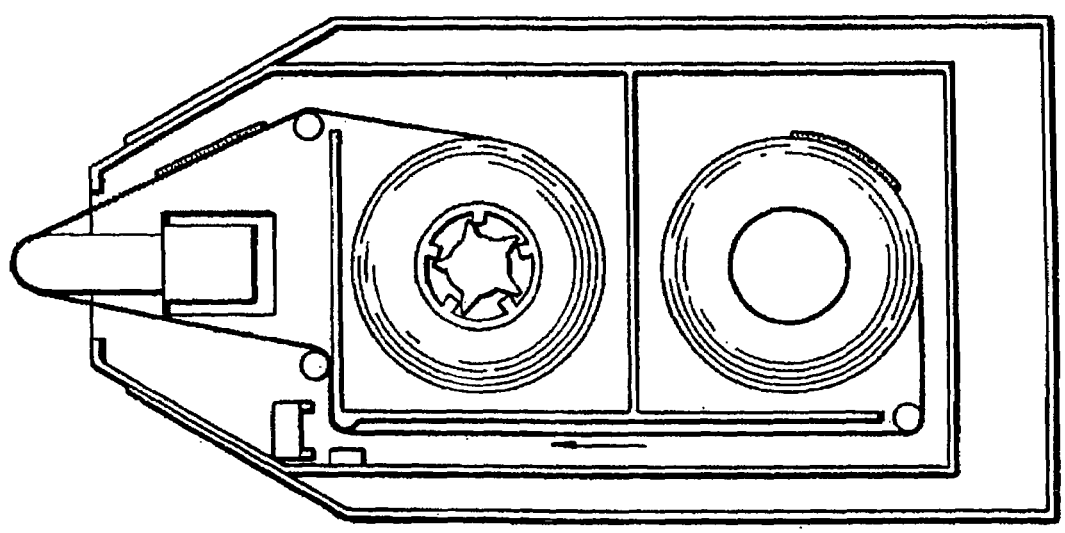

FIG. 9D again is a snapshot taken during the transport of the used test medium into the storage section (50b). When the used test medium is located inside the storage section, the sealing again is closed. As shown in FIG. 9D it is preferred when the distance between two successive test media is so large that a succeeding test medium is still located within the supply section when the preceding test medium is already within the storage section. It is even more preferred when the succeeding test medium is still on the reel, covered by a layer of tape so that it is protected against humidity.

FIG. 10 shows a test media cassette (50) with a supply section (50a) in which a supply reel (57) is being located. The test media tape leaves the supply section via a diffusion channel (70). At the opening of the supply section which is located at the outer end of the diffusion channel a sealing means (80') is located. This sealing means has an axis (81') by which it is rotationally fixed to the housing of the cassette. The sealing means has a sealing section to which an annular gasket (not shown) is fixed. When the cassette is in rest (i.e. no tearing force applied to the tape) the sealing section presses onto a surface surrounding the opening of the cassette (i.e. at the outer end of the diffusion channel in this embodiment). The force to achieve this pressing action is applied to the sealing means (80') via a spring means (59) which integrally belongs to the cassette (non-integral or even spring means not belonging to the cassette may also be contemplated). The integral spring means in the shown case is a nose of plastic material which can be produced in the same production step as the cassette housing (e.g., by injection molding). When the sealing means (80') is assembled, the nose (59) is deformed and spring tension acting onto the sealing means is created by the nose which attempts to get back into unstressed condition. When tape (30) is withdrawn from the supply section the tape needs to be tensioned to overcome the holding forced of the sealing means and/or the friction of the supply reel. As can be seen the sealing means has a rounded section which together with the cassette housing creates a wound channel in which the tape runs. When the tape is stressed it tries to assume a straight direction and therefore it acts on the rounded section of the sealing means so as to move the sealing means against the force of the spring means (59). This movement opens the sealing and lets the test media tape pass through. FIG. 10 further shows a chamber connected to the supply section which is filled with a drying agent (71), which is a molecular sieve in the depicted case.

FIG. 11 shows the hydraulic sealing concept. The housing has an upper section 100a and one lower section (100b) which form a channel at the outlet of the storage section through which the test media tape runs. Within this channel region, there is located a pouch 105 filled with fluid. The pouch is made of a flexible material (e.g., polyethylene) which in its rest position has the shape as depicted in FIG. 11. In this position, the channel is opened so that test media tape can be withdrawn from the supply section and test media (31) can pass through. When pressure is applied to a portion of the pouch located outside the channel, the portion of the pouch located in the channel region expands and form fittingly engages the tape within the channel. Pressure application can e.g. be made by a stamp (110). For obtaining a tight sealing of the supply section against humidity, the channel is closed by the pouch when no unused test media are to be withdrawn. In this closed position, a free tape region between two successive test media is located in the channel and is form fittingly sealed by the hydraulic sealing means.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A body fluid testing device for analyzing a body fluid, comprising:
a test media tape adapted to collect the body fluid, said test media tape comprising a tape and test media portions, wherein a free tape portion without test medium is located between successive test media portions, said testing device further comprising a supply portion, wherein said supply portion comprises a housing in which uncontaminated test media tape is contained, said housing further having an opening for withdrawing test media tape from the housing, said supply portion further having a sealing means for closing said opening against the surrounding, wherein a free tape portion of said test media tape is located between a surface of the housing and the sealing means when said sealing means closes said opening, wherein the sealing means includes a deformable gasket, wherein said deformable gasket has a first and a second lip of sealing material, wherein said first lip is inclined apart from said opening and said second lip is inclined towards said opening, and wherein said sealing means has a lever for opening the sealing of the housing, the lever being actuated by tension applied to the test media tape.

2. A body fluid testing device according to claim 1, wherein said tape in said free tape portion has a thickness of less than 100 micrometers.

3. A body fluid testing device according to claim 1, wherein the gasket has a shore hardness of less than 70.

4. A body fluid testing device according to claim 1, wherein said housing has an internal channel which is the sole air connection between a storage portion of said housing and the surrounding and said test media tape runs through said channel when leaving the housing via the opening of the housing.

5. A body fluid testing device according to claim 4, wherein the length of said channel is equal or shorter than the length of a free tape portion between successive test media.

6. A body fluid testing device according to claim 1, wherein said supply portion is a removable cassette.

7. The device of claim 1 further comprising a sensor for sensing a change of a test medium induced by reaction with said body fluid.

8. The device of claim 1, wherein the sealing means can assume a first position in which the sealing means closes the opening of the container and a second position in which the opening is opened so that test media tape can be withdrawn out of the housing.

9. Body fluid testing device according to claim 1, wherein the sealing means is a form fitting sealing means.

10. A body fluid testing device for analyzing a body fluid, comprising:
a test media tape adapted to collect the body fluid,
said test media tape comprising a tape and test media portions, wherein a free tape portion without test medium is located between successive test media portions,
said testing device further comprising a supply portion,
wherein said supply portion comprises a housing in which uncontaminated test media tape is contained, said housing further having an opening for withdrawing test media tape from the housing,
said supply portion further having a sealing means for closing said opening against the surrounding, wherein a free tape portion of said test media tape is located between a surface of the housing and the sealing means when said sealing means closes said opening, and
wherein said sealing means is a hydraulic sealing means, a pouch filled with fluid positioned to seal against the test media tape when pressurized.

11. The device of claim 10, in which the hydraulic sealing means includes:
a stamp configured to press against the pouch to pressurize the pouch.

* * * * *